United States Patent [19]

Alexandrovich et al.

[11] Patent Number: 5,075,190

[45] Date of Patent: Dec. 24, 1991

[54] TONERS AND DEVELOPERS CONTAINING N-SUBSTITUTED PYRIDINIUM SALTS AS CHARGE CONTROL AGENTS

[75] Inventors: Peter S. Alexandrovich, Rochester; Alexandra D. Bermel, Spencerport; Zona R. Pierce; John C. Wilson, both of Rochester, all of N.Y.

[73] Assignee: Eastman Kodak Company, Rochester, N.Y.

[21] Appl. No.: 560,644

[22] Filed: Jul. 31, 1990

[51] Int. Cl.$^5$ .............................................. G03G 9/08
[52] U.S. Cl. ................................. 430/110; 430/115
[58] Field of Search ............................... 430/110, 115

[56] References Cited

U.S. PATENT DOCUMENTS

| | | | |
|---|---|---|---|
| Re. 32,883 | 3/1989 | Lu | 430/110 |
| 4,139,483 | 2/1979 | Williams et al. | 252/62.1 P |
| 4,298,672 | 11/1981 | Lu | 430/108 |
| 4,338,390 | 7/1982 | Lu | 430/110 |
| 4,394,430 | 7/1983 | Jadwin et al. | 430/110 |
| 4,490,455 | 12/1984 | Hoffend et al. | 430/110 |
| 4,684,596 | 8/1987 | Bonser et al. | 430/110 |
| 4,789,614 | 12/1988 | Bugner et al. | 430/110 |
| 4,803,017 | 2/1989 | Bugner et al. | 260/501.15 |
| 4,806,283 | 2/1989 | Bugner et al. | 260/501.15 |
| 4,806,284 | 2/1989 | Bugner et al. | 260/501.15 |
| 4,812,378 | 3/1989 | Bugner et al. | 260/501.15 |
| 4,812,380 | 3/1989 | Bugner et al. | 260/501.15 |
| 4,812,381 | 3/1989 | Bugner et al. | 260/501.15 |
| 4,834,920 | 5/1989 | Bugner et al. | 260/501.15 |
| 4,834,921 | 5/1989 | Bugner et al. | 260/501.15 |
| 4,840,864 | 6/1989 | Bugner et al. | 260/501.15 |
| 4,851,561 | 7/1989 | Bugner et al. | 560/14 |
| 4,954,414 | 9/1990 | Adair et al. | 430/917 X |

*Primary Examiner*—David Welsh
*Attorney, Agent, or Firm*—Willard G. Montgomery

[57] ABSTRACT

New electrostatographic toners and developers are provided containing new charge-control agents comprising N-substituted pyridinium salts having the

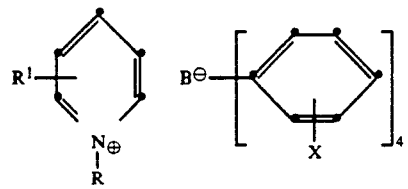

wherein R is a straight or branched chain alkyl group having from 1 to 24 carbon atoms, aralkyl in which the alkyl group has 1 to 20 carbon atoms and the aryl group has from 6 to 14 carbon atoms, $R^1$ is hydrogen or a straight or branched chain alkyl or alkoxy group having from 1 to 24 carbon atoms, aralkyl or alkaryl in which the alkyl group has 1 to 20 carbon atoms and the aryl group has from 6 to 14 carbon atoms, unsubstituted aryl having from 6 to 14 carbon atoms or aryl having from 6 to 14 carbon atoms substituted with one or more nitro, alkoxy or halo groups and X is hydrogen, chlorine, bromine, fluorine or iodine.

20 Claims, No Drawings

TONERS AND DEVELOPERS CONTAINING N-SUBSTITUTED PYRIDINIUM SALTS AS CHARGE CONTROL AGENTS

FIELD OF THE INVENTION

This invention relates to certain new electrostatographic toners and developers containing new N-substituted pyridinium salts as charge-control agents. More particularly, the new salts are thermally stable salts that can be well-dispersed in typical toner binder materials to form the inventive toners having good charging properties and improved humidity insensitivity.

BACKGROUND OF THE INVENTION

In electrostatography an image comprising an electrostatic field pattern, usually of non-uniform strength, (also referred to as an electrostatic latent image) is formed on an insulative surface of an electrostatographic element by any of various methods. For example, the electrostatic latent image may be formed electrophotographically (i.e., by imagewise photo-induced dissipation of the strength of portions of an electrostatic field of uniform strength previously formed on a surface of an electrophotographic element comprising a photoconductive layer and an electrically conductive substrate), or it may be formed by dielectric recording (i.e., by direct electrical formation of an electrostatic field pattern on a surface of a dielectric material). Typically, the electrostatic latent image is then developed into a toner image by contacting the latent image with an electrostatographic developer. If desired, the latent image can be transferred to another surface before development.

One well-known type of electrostatographic developer comprises a dry mixture of toner particles and carrier particles. Developers of this type are commonly employed in well-known electrostatographic development processes such as cascade development and magnetic brush development. The particles in such developers are formulated such that the toner particles and carrier particles occupy different positions in the triboelectric continuum, so that when they contact each other during mixing to form the developer, they become triboelectrically charged, with the toner particles acquiring a charge of one polarity and the carrier particles acquiring a charge of the opposite polarity. These opposite charges attract each other such that the toner particles cling to the surfaces of the carrier particles. When the developer is brought into contact with the latent electrostatic image, the electrostatic forces of the latent image (sometimes in combination with an additional applied field) attract the toner particles, and the toner particles are pulled away from the carrier particles and become electrostatically attached imagewise to the latent image-bearing surface. The resultant toner image can then be fixed in place on the surface by application of heat or other known methods (depending upon the nature of the surface and of the toner image) or can be transferred to another surface, to which it then can be similarly fixed.

A number of requirements are implicit in such development schemes. Namely, the electrostatic attraction between the toner and carrier particles must be strong enough to keep the toner particles held to the surfaces of the carrier particles while the developer is being transported to and brought into contact with the latent image, but when that contact occurs, the electrostatic attraction between the toner particles and the latent image must be even stronger, so that the toner particles are thereby pulled away from the carrier particles and deposited on the latent image-bearing surface. In order to meet these requirements for proper development, the level of electrostatic charge on the toner particles should be maintained within an adequate range.

The toner particles in dry developers often contain material referred to as a charge agent or charge-control agent, which helps to establish and maintain toner charge within an acceptable range. Many types of charge-control agents have been used and are described in the published patent literature.

One general type of known charge-control agent comprises a quaternary ammonium salt. While many such salts are known, some do not perform an adequate charge-control function in any type of developer, some perform the function well in only certain kinds of developers, and some control charge well but produce adverse side effects.

A number of quaternary ammonium salt charge-control agents are described, for example, in U.S. Pat. Nos. 4,684,596; 4,394,430; 4,338,390; 4,490,455; and 4,139,483. Unfortunately, many of those known charge-control agents exhibit one or more drawbacks in some developers.

For example, some of the known quaternary ammonium salt charge agents lack thermal stability and, thus, totally or partially decompose during attempts to mix them with known toner binder materials in well-known processes of preparing toners by mixing addenda with molten toner binders. Such processes are often referred to as melt-blending or melt-compounding processes and are commonly carried out at temperatures ranging from about 120° to about 200° C. Thus, charge agents that are thermally unstable at temperatures at or below 200° C. can exhibit this decomposition problem.

Also, some known quaternary ammonium salt charge agents exhibit high sensitivity to changes in environmental relative humidity and/or temperature, which can lead to erratic performance of the charge agents under changing environmental conditions.

It would, therefore, be desirable to provide new dry electrographic toners and developers containing N-substituted pyridinium salts that could perform the charge-controlling function well, while avoiding or minimizing the drawbacks noted above. The present invention does this.

SUMMARY OF THE INVENTION

The invention provides new, dry, particulate electrostatographic toners and developers containing new charge-control agents comprising N-substituted pyridinium salts having the structure

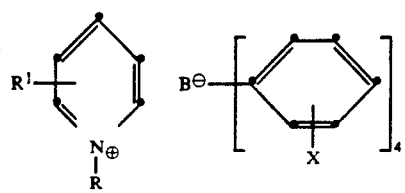

wherein R is a straight or branched chain alkyl group having from 1 to 24 carbon atoms, aralkyl in which the alkyl group has 1 to 20 carbon atoms and the aryl group has from 6 to 14 carbon atoms, $R^1$ is hydrogen or a straight or branched chain alkyl or alkoxy group having from 1 to 24 carbon atoms, aralkyl or alkaryl in which the alkyl group has 1 to 20 carbon atoms and the aryl group has from 6 to 14 carbon atoms, unsubstituted aryl having from 6 to 14 carbon atoms or aryl having from 6 to 14 carbon atoms substituted with one or more nitro, alkoxy or halo groups and X is hydrogen, chlorine, bromine, fluorine or iodine.

The inventive toners comprise a polymeric binder and a charge-control agent chosen from the salts defined above. The inventive developers comprise carrier particles and the inventive particulate toner defined above.

The salts provide good charge-control in the inventive toners and developers. The inventive toners and developers do not exhibit unacceptably high environmental sensitivity and have decomposition points well above 200° C.

DESCRIPTION OF THE PREFERRED EMBODIMENTS

The new N-substituted pyridinium salts employed in the toners and developers of the invention can be conveniently prepared from readily available starting materials, such as a halide salt of the appropriate N-substituted pyridinium and an alkali metal salt of a tetraphenylborate. Optionally, the N-substitutedpyridinium halide may be prepared from an appropriate organic halide and a pyridine or a substituted pyridine. For example, pyridine can be quaternized with 1-bromotetradecane in acetonitrile to give N-tetradecylpyridinium bromide. An aqueous solution of the N-tetradecylpyridinium halide when mixed with an aqueous solution of sodium tetraphenylborate in stoichiometric proportions yields a precipitate of the desired quaternary pyridinium salt.

Illustrative examples of N-substituted pyridinium salts useful in the present invention include, for example, N-ethylpyridinium tetraphenylborate, N-propylpyridinium tetraphenylborate, N-butylpyridinium tetraphenylborate, N-hexylpyridinium tetraphenyl-borate, N-dodecylpyridinium tetraphenylborate, N-tetradecylpyridinium tetraphenylborate, N-hexadecyl-pyridinium tetraphenylborate, N-octadecylpyridinium tetraphenylborate, N-ethylpyridinium tetra(4-chlorophenyl)borate, N-(4-methoxybenzyl)pyridinium tetraphenylborate, N-hexyl-2-methoxypyridinium tetraphenylborate, N-ethylpyridiniumtetra-(3-chlorophenyl)borate, N-hexyl-2-benzylpyridinium tetraphenylborate, N-hexyl-4-benzylpyridinium tetraphenylborate, N-hexyl-2-methylpyridinium tetraphenylborate, and N-(4-nitrobenzyl)-pyridinium tetraphenylborate. A particularly useful N-substituted pyridinium salt is N-dodecylpyridinium tetraphenylborate.

To be utilized as a charge-control agent in the electrostatographic toners of the invention, the N-substituted pyridinium salt is mixed in any convenient manner (as, for example, by melt-blending as described, for example, in U.S. Pat. Nos. 4,684,596 and 4,394,430) with an appropriate polymeric toner binder material and any other desired addenda, and the mix is then ground to desired size to form a free-flowing powder of toner particles containing the charge agent. Other suitable methods of preparing electrostatographic toners comprising the charge-control agents of the present invention include those well known in the art such as spray drying, melt dispersion and dispersion polymerization.

Toner particles of the invention have an average diameter between about 0.1 μm and about 100 μm, a value in the range from about 1.0 to about 30 μm being preferable for many currently used machines. However, larger or smaller particles may be needed for particular methods of development or development conditions.

Generally, it has been found desirable to add from about 0.05 to about 6 parts and preferably 0.05 to about 2.0 parts by weight of the aforementioned pyridinium salts per 100 parts by weight of a polymer to obtain the improved toner composition of the present invention. Although larger or smaller amounts of a charge control agent can be added, it has been found that if amounts much lower than those specified above are utilized, the charge-control agent tends to exhibit little or substantially no improvement in the properties of the toner composition. As amounts more than about 6 parts of the charge-control agent per 100 parts of polymeric binder are added, it has been found that the net toner charge exhibited by the resultant toner composition tends to be reduced. Of course, it must be recognized that the optimum amount of charge-control agent to be added will depend, in part, on the particular N-substituted pyridinium charge-control agent selected and the particular polymer to which it is added. However, the amounts specified hereinabove are typical of a useful range of charge-control agent utilized in conventional dry toner materials.

The polymers useful as toner binders in the practice of the present invention can be used alone or in combination and include those polymers conventionally employed in electrostatic toners. Useful polymers generally have a glass transition temperature within the range of from 50° to 120° C. Preferably, toner particles prepared from these polymers have relatively high caking temperature, for example, higher than about 60° C., so that the toner powders can be stored for relatively long periods of time at fairly high temperatures without having individual particles agglomerate and clump together. The softening point of useful polymers preferably is within the range of from about 65° C. to about 200° C. so that the toner particles can readily be fused to a conventional paper receiving sheet to form a permanent image. Especially preferred polymers are those having a softening point within the range of from about 65° to about 120° C. Of course, where other types of receiving elements are used, for example, metal plates such as certain printing plates, polymers having a softening point and glass transition temperature higher than the values specified above can be used.

Among the various polymers which can be employed in the toner particles of the present invention are polycarbonates, resin-modified maleic alkyd polymers, polyamides, phenol-formaldehyde polymers and various derivatives thereof, polyester condensates, modified alkyd polymers, aromatic polymers containing alternating methylene and aromatic units such as described in U.S. Pat. No. 3,809,554 and fusible crosslinked polymers as described in U.S. Pat. Re No. 31,072.

Typical useful toner polymers include certain polycarbonates such as those described in U.S. Pat. No. 3,694,359, which include polycarbonate materials containing an alkylidene diarylene moiety in a recurring unit and having from 1 to about 10 carbon atoms in the alkyl moiety. Other useful polymers having the above-described physical properties include polymeric esters of acrylic and methacrylic acid such as poly(alkyl acrylate), and poly(alkyl methacrylate) wherein the alkyl moiety can contain from 1 to about 10 carbon atoms. Additionally, other polyesters having the aforementioned physical properties are also useful. Among such other useful polyesters are copolyesters prepared from terephthalic acid (including substituted terephthalic acid), a bis(hydroxyalkoxy)phenylalkane having from 1 to 4 carbon atoms in the alkoxy radical and from 1 to 10 carbon atoms in the alkane moiety (which can also be a halogen-substituted alkane), and an alkylene glycol having from 1 to 4 carbon atoms in the alkylene moiety.

Other useful polymers are various styrene-containing polymers. Such polymers can comprise, e.g., a polymerized blend of from about 40 to about 100 percent by weight of styrene, from 0 to about 45 percent by weight of a lower alkyl acrylate or methacrylate having from 1 to about 4 carbon atoms in the alkyl moiety such as methyl, ethyl, isopropyl, butyl, etc. and from about 5 to about 50 percent by weight of another vinyl monomer other than styrene, for example, a higher alkyl acrylate or methacrylate having from about 6 to 20 or more carbon atoms in the alkyl group. Typical styrene-containing polymers prepared from a copolymerized blend as described hereinabove are copolymers prepared from a monomeric blend of 40 to 60 percent by weight styrene or styrene homolog, from about 20 to about 50 percent by weight of a lower alkyl acrylate or methacrylate and from about 5 to about 30 percent by weight of a higher alkyl acrylate or methacrylate such as ethylhexyl acrylate (e.g., styrene-butyl acrylate-ethylhexyl acrylate copolymer). Preferred fusible styrene copolymers are those which are covalently crosslinked with a small amount of a divinyl compound such as divinylbenzene. A variety of other useful styrene-containing toner materials are disclosed in U.S. Pat. No. 2,918,460; Re 25,316; 2,788,288; 2,638,416; 2,618,552 and 2,659,670.

Various kinds of well-known addenda (e.g., colorants, release agents, etc.) can also be incorporated into the toners of the invention.

Numerous colorant materials selected from dyestuffs or pigments can be employed in the toner materials of the present invention. Such materials serve to color the toner and/or render it more visible. Of course, suitable toner materials having the appropriate charging characteristics can be prepared without the use of a colorant material where it is desired to have a developed image of low optical density. In those instances where it is desired to utilize a colorant, the colorants can, in principle, be selected from virtually any of the compounds mentioned in the Colour Index Volumes 1 and 2, Second Edition.

Included among the vast number of useful colorants are such materials as Hansa Yellow G (C.I. 11680), Nigrosine Spirit soluble (C.I. 50415), Chromogen Black ETOO (C.I. 45170), Solvent Black 3 (C.I. 26150), Fuchsine N (C.I. 42510), C.I. Basic Blue 9 (C.I. 52015). Carbon black also provides a useful colorant. The amount of colorant added may vary over a wide range, for example, from about 1 to about 20 percent of the weight of the polymer. Particularly good results are obtained when the amount is from about 1 to about 10 percent.

To be utilized as toners in the electrostatographic developers of the invention, toners of this invention can be mixed with a carrier vehicle. The carrier vehicles, which can be used with the present toners to form the new developer compositions, can be selected from a variety of materials. Such materials include carrier core particles and core particles overcoated with a thin layer of film-forming resin.

The carrier core materials can comprise conductive, non-conductive, magnetic, or non-magnetic materials. For example, carrier cores can comprise glass beads; crystals of inorganic salts such as aluminum potassium chloride; other salts such as ammonium chloride or sodium nitrate; granular zircon; granular silicon; silicon dioxide; hard resin particles such as poly(methyl methacrylate); metallic materials such as iron, steel, nickel, carborundum, cobalt, oxidized iron; or mixtures or alloys of any of the foregoing. See, for example, U.S. Pat. Nos. 3,850,663 and 3,970,571. Especially useful in magnetic brush development schemes are iron particles such as porous iron particles having oxidized surfaces, steel particles, and other "hard" or "soft" ferromagnetic materials such as gamma ferric oxides or ferrites, such as ferrites of barium, strontium, lead, magnesium, or aluminum. See, for example, U.S. Pat. Nos. 4,042,518; 4,478,925; and 4,546,060.

As noted above, the carrier particles can be overcoated with a thin layer of a film-forming resin for the purpose of establishing the correct triboelectric relationship and charge level with the toner employed. Examples of suitable resins are the polymers described in U.S. Pat. Nos. 3,547,822; 3,632,512; 3,795,618 and 3,898,170 and Belgian Pat. No. 797,132. Other useful resins are fluorocarbons such as polytetrafluoroethylene, poly(vinylidene fluoride), mixtures of these, and copolymers of vinylidene fluoride and tetrafluoroethylene. See, for example, U.S. Pat. Nos. 4,545,060; 4,478,925; 4,076,857; and 3,970,571. Such polymeric fluorohydrocarbon carrier coatings can serve a number of known purposes. One such purpose can be to aid the developer to meet the electrostatic force requirements mentioned above by shifting the carrier particles to a position in the triboelectric series different from that of the uncoated carrier core material, in order to adjust the degree of triboelectric charging of both the carrier and toner particles. Another purpose can be to reduce the frictional characteristics of the carrier particles in order to improve developer flow properties. Still another purpose can be to reduce the surface hardness of the carrier particles so that they are less likely to break apart during use and less likely to abrade surfaces (e.g., photoconductive element surfaces) that they contact during use. Yet another purpose can be to reduce the tendency of toner material or other developer additives to become undesirably permanently adhered to carrier surfaces during developer use (often referred to as scumming). A further purpose can be to alter the electrical resistance of the carrier particles.

A typical developer composition containing the above-described toner and a carrier vehicle generally comprises from about 1 to about 20 percent by weight of particulate toner particles and from about 80 to about 99 percent by weight carrier particles. Usually, the carrier particles are larger than the toner particles. Conventional carrier particles have a particle size on the order of from about 20 to about 1200 microns, preferably 30-300 microns.

Alternatively, the toners of the present invention can be used in a single component developer, i.e., with no carrier particles.

The toner and developer compositions of this invention can be used in a variety of ways to develop electrostatic charge patterns or latent images. Such developable charge patterns can be prepared by a number of means and be carried for example, on a light sensitive photoconductive element or a non-light-sensitive dielectric-surfaces element such as an insulator-coated conductive sheet. One suitable development technique involves cascading the developer composition across the electrostatic charge pattern, while another technique involves applying toner particles from a magnetic brush. This latter technique involves the use of a magnetically attractable carrier vehicle in forming the developer composition. After imagewise deposition of the toner particles, the image can be fixed, e.g., by heating the toner to cause it to fuse to the substrate carrying the toner. If desired, the unfused image can be transferred to a receiver such as a blank sheet of copy paper and then fused to form a permanent image.

The following examples are presented to further illustrate some preferred embodiments of the toners and developers of the invention and the charge agent salts employed therein, and to compare their properties and performance to those of salts, toners, and developers outside the scope of the invention.

EXAMPLE 1—PREPARATION OF N-ETHYLPYRIDINIUM TETRAPHENYLBORATE

A solution of N-ethylpyridinium bromide (18.8 g; 0.10 mol) in 190 mL of water was added to a solution of sodium tetraphenylborate (34.2 g; 0.10 mol) in 340 mL of water. A white precipitate immediately formed. The mixture was stirred for 30 minutes and filtered. The solid was washed with water and then with methanol and dried in a vacuum oven. The solid was recrystallized from 2-butanone to yield 25.3 g (59.2%) of product; m.p.=209°-212° C. The product, N-ethylpyridinium tetraphenylborate, was characterized by a combination of elemental analysis, nuclear magnetic resonance spectroscopy, melting point and thermogravimetric analysis. Elemental analysis calculated for $C_{31}H_{30}BN$ (437.40): 87.1% C, 7.1% H, 2.5% B and 3.3% N. Found: 87.5% C, 7.0% H, 2.4% B, and 3.2% N. TGA (10° C./min; air): stable to 242° C. NMR (DMSO): 81.49 (t, 3H), 4.53 (q, 2H), 6.59-7.36 (m, 20H), 7.89-8.13 (m, 2H), 8.32-8.57 (m, 2H).

The other salts within the scope of the invention are prepared similarly.

EXAMPLE 2—PREPARATION OF N-PROPYLPYRIDINIUM TETRAPHENYLBORATE

The general procedure of Example 1 was repeated except that a solution of N-propylpyridinium bromide (97.6 g; 0.48 mol) in 976 mL of water and a solution of sodium tetraphenylborate (165.3 g; 0.48 mol) in 1653 mL of water was used to prepare 95.5 g (45.1%) of N-propylpyridinium tetraphenylborate: m.p. 154°-157° C.; TGA (10° C./min; air): stable to 253° C. Analysis calculated for $C_{32}H_{32}BN$ (441.42); 87.1% C, 7.3% H, 2.4% B and 3.2% N. Found: 86.6% C, 7.3% H, 1.8% B and 3.1% N.

EXAMPLE 3—PREPARATION OF N-BUTYL PYRIDINIUM TETRAPHENYLBORATE

The general procedure of Example 1 was repeated except that a solution of N-butylpyridinium bromide (108.1 g; 0.50 mol) in 1081 mL of water and a solution of 172.1 g (0.50 mol) of sodium tetraphenylborate in 1721 mL of water was used to prepare 145.0 g (63.7%) of N-butylpyridinium tetraphenylborate: m.p. 158°-160° C.; TGA (10° C./min; air): stable to 242° C. Analysis calculated for $C_{33}H_{34}BN$ (455.45); 87.0% C, 7.5% H, 2.4% B and 3.1% N. Found: 86.6% C, 7.6% H, 2.3% B and 3.3% N.

EXAMPLE 4—PREPARATION OF N-PENTYLPYRIDINIUM TETRAPHENYLBORATE

The general procedure of Example 1 was repeated except that a solution of N-pentylpyridinium bromide (137.8 g; 0.60 mol) in 1378 mL of water and a solution of sodium tetraphenylborate (204.9 g; 0.60 mol) in 2049 mL of water was used to prepare 207.0 g (73.4%) of N-pentylpyridinium tetraphenylborate: m.p. 170°-172° C.; TGA (10° C./min; air): stable to 244° C. Analysis calculated for $C_{34}H_{36}BN$ (469.49); 87.0% C, 7.7% H, 2.3% B and 3.0% N. Found: 87.4% C, 7.7% H, 2.2% B and 3.0% N.

EXAMPLE 5—PREPARATION OF N-HEXYLPYRIDINIUM TETRAPHENYLBORATE

The general procedure of Example 1 was repeated except that a solution of N-hexylpyridinium bromide (138.6 g; 0.57 mol) in 1386 mL of water and a solution of sodium tetraphenylborate (194.3 g; 0.57 mol) in 1943 mL of water was used to prepare 176.7 g (64.4%) of N-hexylpyridinium tetraphenylborate:m.p. 155°-157° C.; TGA (10° C./min; air): stable to 248° C. Analysis calculated for $C_{35}H_{38}BN$ (483.50); 86.9% C, 7.9% H, 2.2% B and 2.9% N. Found: 87.0% C, 7.9% H, 2.0% B and 3.2% N.

EXAMPLE 6—PREPARATION OF N-DODECYLPYRIDINIUM TETRAPHENYLBORATE

The general procedure of Example 1 was repeated except that a solution of N-dodecyl pyridinium bromide (50.0 g; 0.153 mol) in 500 mL of water and a solution of sodium tetraphenylborate (52.2 g; 0.153 mol) in 522 mL of water was used to prepare 43.0 g (49%) of N-dodecylpyridinium tetraphenylborate:m.p. 109°-110° C.; TGA (10°/min; air): stable to 212° C. Analysis calculated for $C_{41}H_{50}BN$ (567.67); 86.7% C, 8.9% H, 1.9% B and 2.5% N. Found: 87.3% C, 8.8% H, 2.0% B and 2.5% N.

EXAMPLE 7—PREPARATION OF N-TETRADECYLPYRIDINIUM TETRAPHENYLBORATE

The general procedure of Example 1 was repeated except that a solution of N-tetradecylpyridinium bromide (50.0 g; 0.14 mol) in 500 mL of water and a solution of sodium tetraphenylborate (47.9 g; 0.14 mol) in 479 mL of water was used to prepare 35.7 g (42.8%) of N-tetradecylpyridinium tetraphenylborate; m.p. 91°-92° C.; TGA (10° C./min; air): stable to 238° C. Analysis calculated for $C_{43}H_{54}BN$ (595.72); 86.7% C, 9.1% H, 1.8% B and 2.4% N. Found: 87.1% C, 9.1% H, 1.8% B and 2.2% N.

EXAMPLE 8—PREPARATION OF N-HEXADECYLPYRIDINIUM TETRAPHENYLBORATE

The general procedure of Example 1 was repeated except that a solution of N-hexadecylpyridinium bromide (19.22 g; 0.05 mol) in 150 mL of water and a solution of sodium tetraphenylborate (17.11 g; 0.05 mol) in 50 mL of water was used to prepare 10.0 g (32.1%) of N-hexadecylpyridinium tetraphenylborate:m.p. 87°-89°

C.; TGA (10° C./min; air): stable to 250° C. Analysis calculated for $C_{45}H_{58}BN$ (623.78); 86.6% C, 9.4% H, 1.7% B and 2.2% N. Found: 86.5% C, 9.2% H, 1.7% B and 2.1% N.

EXAMPLE 9—PREPARATION OF N-OCTADECYLPYRIDINIUM TETRAPHENYLBORATE

The general procedure of Example 1 was repeated except that a solution of N-octadecylpyridinium bromide (50.0 g; 0.121 mol) in 500 mL of water and a solution of sodium tetraphenylborate (41.5 g; 0.121 mol) in 415 mL of water was used to prepare 40.5 g (51.3%) of N-octadecylpyridinium tetraphenylborate:m.p. 88°-90° C.; TGA (10° C./min; air): stable to 248° C. Analysis calculated for $C_{47}H_{62}BN$ (651.83); 86.6% C, 9.6% H, 1.7% B and 2.1% N. Found: 87.0% C, 9.5% H, 1.6% B and 2.2% N.

EXAMPLE 10—SALT DECOMPOSITION POINT

The N-substituted pyridinium salts of Examples 1–9 were compared to quaternary ammonium salts outside the scope of the present invention in regard to decomposition point. Decomposition temperatures were determined by thermal gravimetric analysis (TGA) measured on a DuPont 1090 thermal analyzer equipped with a 951 thermal gravimetric analyzer (10° C./min; air). A sample of known weight is placed in the thermal analyzer and its weight is monitored while the temperature is raised at a constant rate, in this case 10° C./min. The temperature at which significant weight loss begins to occur is taken as the decomposition temperature. Results are presented in Table 1.

TABLE 1

| Salt | Of the Invention | Decomposition Point (°C.) |
|---|---|---|
| N-ethylpyridinium tetraphenylborate | Yes | 242 |
| N-propylpyridinium tetraphenylborate | Yes | 253 |
| N-butylpyridinium tetraphenylborate | Yes | 242 |
| N-pentylpyridinium tetraphenylborate | Yes | 244 |
| N-hexylpyridinium tetraphenylborate | Yes | 248 |
| N-dodecylpyridinium tetraphenylborate | Yes | 212 |
| N-tetradecylpyridinium tetraphenylborate | Yes | 238 |
| N-hexadecylpyridinium tetraphenylborate | Yes | 250 |
| N-octadecylpyridinium tetraphenylborate | Yes | 248 |
| N-benzyl-N,N-dimethyloctadecylammonium chloride | No | 160 |
| N-(p-nitrobenzyl)-N,N-dimethyloctadecylammonium chloride | No | 189 |

The data in Table 1 show that the salts useful in toners of the invention have a decomposition point well above 200° C., whereas the non-inventive salts have a decomposition point below 200° C. indicating likely decomposition of the latter during some toner melt-blending processes.

EXAMPLE 11—CHARGE LEVEL STABILITY VERSUS RELATIVE HUMIDITY CHANGES

The following example compares a developer composition comprising a charge-control agent of the present invention to developer compositions of the prior art containing conventional quaternary ammonium salt charge-control agents with respect to the stability of the charge to mass ratio of the toner as a function of relative humidity. The toner of the present invention included, as a charge-control agent, N-dodecylpyridinium tetraphenylborate, prepared as described in Example 6 above, and the prior art toners contained, as a charge-control agent, N-octadecyl-N,N-dimethylbenzylammonium nitrobenzene sulfonate and tetrabutylammonium triflate. The toners were prepared by a polymer suspension process known to the art as the limited coalescence process as described in U.S. Pat. No. 4,833,060. The concentration of charge agent in the toner was 0.2494 percent by weight based on the total weight of the toner in all cases and each toner contained in addition to the charge agent, 12.469 percent by weight based on the total weight of toner of a cyan phthalocyanine pigment dispersed in a styrene-acrylic resin mixture. Specifically, 75 parts by weight of an 80% styrene—20% butylacrylate copolymer sold by Hercules, Inc., under the trade name Piccotoner 1221 was dissolved together with about 12.5 parts by weight of a cyan phthalocyanine pigment dispersed in 12.5 parts by weight of either a styrene-acrylic resin sold by Goodyear, Inc., under the trade name Pliotone 4003 or a styrene-acrylic resin sold by Goodyear, Inc., under the trade name Pliotone 2102 and 0.25 parts by weight of charge agent in about 400 parts by weight of ethyl acetate. The solution had a solids content of about 20% by weight, based on the total weight of the solution, the pigment content being about 12.469% by weight of the total solids content and the charge agent being about 0.2494% by weight of the total solids content.

About 100 parts by weight of the above solution was added to 305 parts by weight of an aqueous solution buffered to a pH of about 4 (phthalate buffer) containing about 5 parts by weight of a particulate stabilizer comprising 50% silica having a particle size of about 20–25 nanometers, this material being sold under the designation Ludox TM by the duPont Company and about 1.5 parts by weight of a 10 percent solution of poly(adipic acid-co-methylaminoethanol). Upon addition of the styrene butylacrylate copolymer/solvent organic phase to the aqueous suspension, the system was immediately subjected to shear using a Polytron sold by Brinkmann followed by a Microfluidizer sold by Microfluidics, Inc., to form droplets consisting of the polymer, charge agent and pigment dispersion. Upon exiting the Microfluidizer, the solvent was allowed to evaporate by stirring under a stream of nitrogen. The particles were then filtered and treated overnight in a 1N aqueous potassium hydroxide solution followed by another overnight treatment in a 0.1N potassium hydroxide solution to dissolve away the particulate stabilizer (i.e., the silica). The particles were then washed on a filter (distilled water) until neutral pH was obtained and dried. The particles formed had a particle size ranging from 3 to 5 μm. Particle size, as used herein, refers to median volume weighted diameter as measured by conventional diameter measuring devices such as the Coulter Multisizer, sold by Coulter, Inc. Median volume weighted diameter, as defined herein, is the size at which one-half of the volume of the sample is composed of particles larger than the median size and one-half of the volume of the sample is composed of particles smaller than the median size. Developer compositions were then prepared by blending together 7 parts by weight of each of the toners thus prepared and 93 parts by weight of strontium ferrite carrier particles and (b) 10 parts by weight of each of the toners thus prepared and 90 parts by weight of the strontium ferrite carrier particles. The ferrite carrier particles were thinly coated with about 1.5% of a polymethylmethacrylate resin available from Soken, Inc. under the trade name Soken 1201 and 0.5% of a polyvinylidene fluoride resin available from Pennwalt Co. under the trade name Kynar 301F, except for the carrier particles present in the developer compositions containing tetrabutylammonium triflate as the charge-control agent in the toner in which case the ferrite carrier particles were coated with 2%, Kynar 301F alone. The developers were shaken for one minute and separately aged at low (about 15) relative humidity at 82° F., medium (about 50%) relative humidity at 72° F., and higher (about 82%) relative humidity at 72° F. for one hour. The triboelectric charge of the toner (charge to mass ratio) was measured by a method whereby the toner charge in the developer compositions, as indicated in microcoulombs per gram of toner particles ($\mu c/g$), was determined by plating the toner by electrical bias (300 volts) from a rotating-core magnetic brush applicator (core rotation =1500 revolutions per minute) of the developer (0.3 g sample) onto the electrically insulating layer of a test element. The element was composed of, in sequence, a film support, an electrically conducting layer and the insulating layer. The test element was connected via the conducting layer to an electrometer and the charge was measured during the plating (i.e., toning) operation. The registered charge was divided by the weight of the toner plated onto the element to obtain the charge per mass of toner.

The results are listed in Table II below and show the percentage decrease of the triboelectric charge from 15% to 82% relative humidity.

TABLE II

| Charge Agent | Charge Agent Conc. (pph) | Toner Conc. | % Drop in Q/M ($\mu coul/g$) from 15% to 82% RH |
|---|---|---|---|
| N-dodecylpyridinium tetraphenylborate[a] | 0.25 | 7 | 6.9%[c] |
| N-dodecylpyridinium tetraphenylborate[a] | 0.25 | 10 | 6.4% |
| tetrabutylammonium triflate[a] | 0.25 | 7 | 40.0%[c] |
| tetrabutylammonium triflate[a] | 0.25 | 10 | 33.3% |
| N-octadecyl-N,N-dimethylbenzyl-ammonium nitrobenzenesulfonate[b] | 0.25 | 7 | 12.9%[c] |
| N-octadecyl-N,N-dimethylbenzyl-ammonium nitrobenzenesulfonate[b] | 0.25 | 10 | 22.6% |

[a] = charge agent dispersed in Pliotone 2102
[b] = charge agent dispersed in Pliotone 4003
[c] = average of three measurements From the table, it can be seen that the charge control agent of the invention, i.e., N-dodecylpyridinium tetraphenylborate provided the most stable performance.

The invention has been described in detail with particular reference to preferred embodiments thereof, but it will be understood that variations and modifications can be effected within the spirit and scope of the invention.

What is claimed is:

1. A dry, particulate, electrostatographic toner composition comprising a polymeric binder and a charge control agent comprising an N-substituted pyridinium salt having the structure

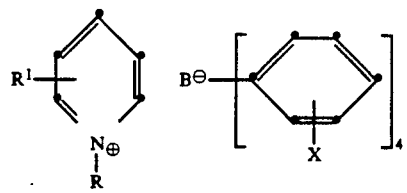

wherein R is a straight or branched chain alkyl group having from 1 to 24 carbon atoms, aralkyl in which the alkyl group has 1 to 20 carbon atoms and the aryl group has from 6 to 14 carbon atoms, $R^1$ is hydrogen or a straight or branched chain alkyl or alkoxy group having from 1 to 24 carbon atoms, aralkyl or alkaryl in which the alkyl group has 1 to 20 carbon atoms and the aryl group has from 6 to 14 carbon atoms, unsubstituted aryl having from 6 to 14 carbon atoms or aryl having from 6 to 14 carbon atoms substituted with one or more nitro, alkoxy or halo groups and X is hydrogen, chlorine, bromine, fluorine or iodine.

2. The toner composition of claim 1, wherein said salt is N-ethylpyridinium tetraphenylborate.

3. The toner composition of claim 1, wherein said salt is N-propylpyridinium tetraphenylborate.

4. The toner composition of claim 1, wherein said salt is N-butylpyridinium tetraphenylborate.

5. The toner composition of claim 1, wherein said salt is N-pentylpyridinium tetraphenylborate.

6. The toner composition of claim 1, wherein said salt is N-hexylpyridinium tetraphenylborate.

7. The toner composition of claim 1, wherein said salt is N-dodecylpyridinium tetraphenylborate.

8. The toner composition of claim 1, wherein said salt is N-tetradecylpyridinium tetraphenylborate.

9. The toner composition of claim 1, wherein said salt is N-hexadecylpyridinium tetraphenylborate.

10. The toner composition of claim 1, wherein said salt is N-octadecylpyridinium tetraphenylborate.

11. The toner composition of claim 1, wherein said salt is N-ethylpyridinium tetra(4-chlorophenyl)borate.

12. The toner composition of claim 1, wherein said salt is N-(4-methoxybenzyl)pyridinium tetraphenylborate.

13. The toner composition of claim 1, wherein said salt is N-hexyl-2-methoxypyridinium tetraphenylborate.

14. The toner composition of claim 1, wherein said salt is N-ethylpyridinium tetra(3-chlorophenyl)borate.

15. The toner composition of claim 1, wherein said salt is N-hexyl-2-benzylpyridinium tetraphenylborate.

16. The toner composition of claim 1, wherein said salt is N-hexyl-4-benzylpyridinium tetraphenylborate.

17. The toner composition of claim 1, wherein said salt is N-hexyl-2-methylpyridinium tetraphenylborate.

18. The toner composition of claim 1, wherein said salt is N-(4-nitrobenzyl)pyridinium tetraphenylborate.

19. An electrostatographic developer comprising:
a. the particulate toner composition of claim 1 and
b. carrier particles.

20. The developer of claim 19, wherein the carrier particles comprise core material coated with a fluorohydrocarbon polymer.

* * * * *